United States Patent [19]

Katsaros et al.

[11] Patent Number: 4,973,313
[45] Date of Patent: Nov. 27, 1990

[54] OVER THE NEEDLE CATHETER INTRODUCER

[75] Inventors: Georges Katsaros, Jupille; Paul Macors; Giancarlo Polese, both of Liege, all of Belgium

[73] Assignee: Sherwood Medical Company, St. Louis, Mo.

[21] Appl. No.: 406,649

[22] Filed: Sep. 13, 1989

[51] Int. Cl.$^5$ ............................................. A61M 5/00
[52] U.S. Cl. .................................................. 604/165
[58] Field of Search ............... 604/165, 164, 162, 167, 604/283

[56] References Cited

U.S. PATENT DOCUMENTS

| | | |
|---|---|---|
| 3,568,679 | 3/1971 | Reif . |
| 3,714,945 | 2/1973 | Stanley . |
| 3,739,778 | 6/1973 | Monestere, Jr. et al. . |
| 3,853,130 | 12/1974 | Sheridan . |
| 4,013,080 | 3/1977 | Froning . |
| 4,191,186 | 3/1980 | Keeler . |
| 4,191,305 | 3/1980 | Serberg . |
| 4,209,015 | 6/1980 | Wicks . |
| 4,230,123 | 10/1980 | Hawkins, Jr. . |
| 4,292,970 | 10/1981 | Hession, Jr. . |
| 4,311,137 | 1/1982 | Gerard . |
| 4,362,156 | 12/1982 | Feller, Jr. et al. ................... 604/165 |
| 4,445,893 | 5/1984 | Bodicky ............................... 604/165 |
| 4,496,348 | 1/1985 | Genese et al. ...................... 604/167 |
| 4,504,269 | 3/1985 | Durand ................................ 604/272 |
| 4,565,544 | 1/1986 | Muller et al. ....................... 604/164 |
| 4,711,636 | 12/1987 | Bierman ............................... 604/180 |
| 4,790,817 | 12/1988 | Luther .................................. 604/53 |
| 4,828,549 | 5/1989 | Kvalo .................................. 604/164 |
| 4,834,708 | 5/1989 | Pillari ................................... 604/165 |

OTHER PUBLICATIONS

Acta Radiologica, vol. 39/Jan.–Jun. 1953, Sven Icar Seldinger entitled, "Catheter Replacement of the Needle in Percutaneous Arteriography", pp. 368-376.

Primary Examiner—Stephen C. Pellegrino
Attorney, Agent, or Firm—Andrew J. Beck; Montgomery W. Smith; Richard D. Allison

[57] ABSTRACT

An over the needle catheter introducer having an introducer needle and a cannula member with finger engaging means on the introducer needle and cannula member and a groove means on the introducer means to selectively engage a luer extension on the proximal end of the cannula member so that the introducer needle engages the cannula member in one position and is readily released therefrom by rotation of the cannula member about the introducer needle.

11 Claims, 3 Drawing Sheets

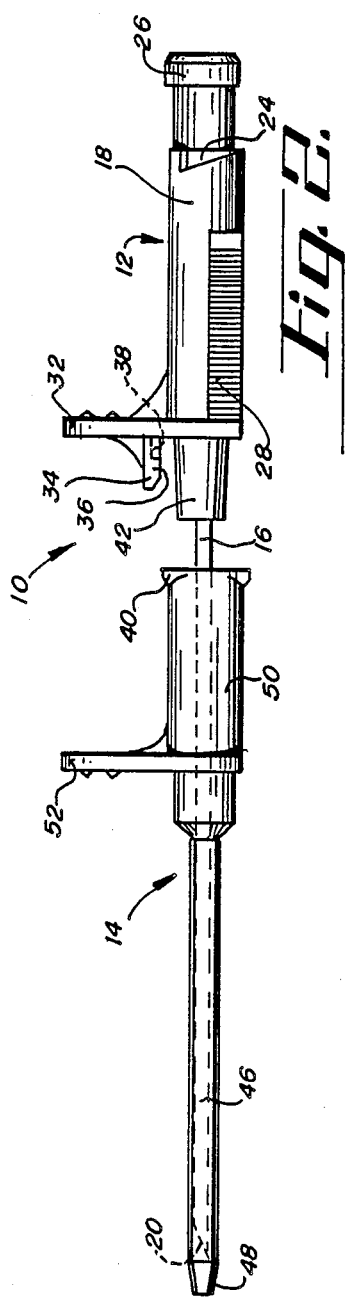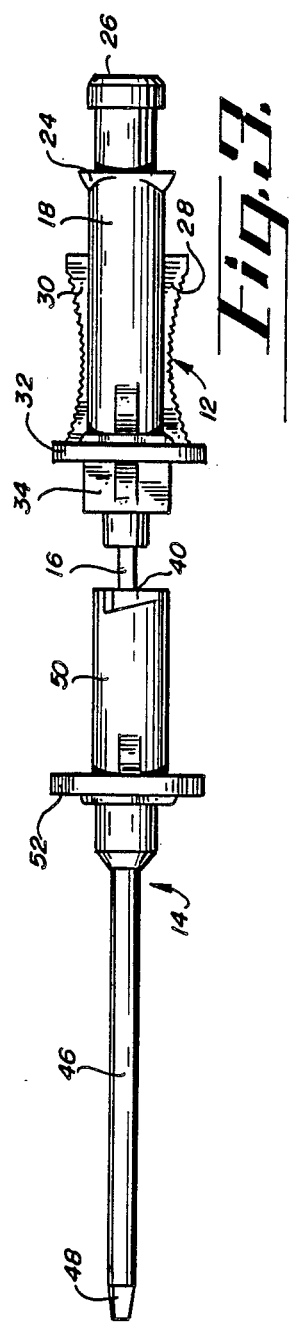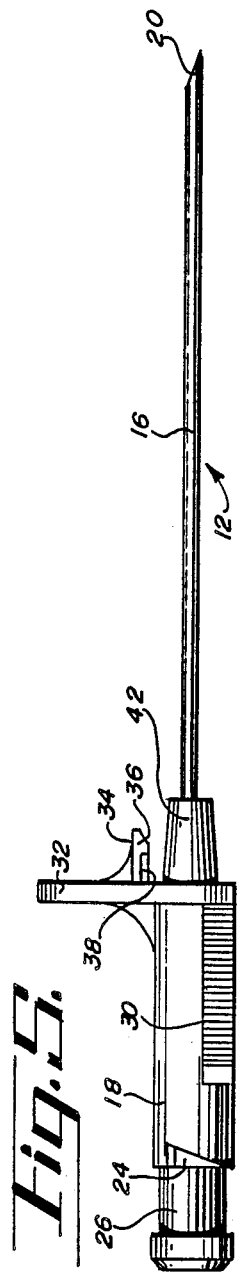

OVER THE NEEDLE CATHETER INTRODUCER

FIELD OF THE INVENTION

The present invention relates generally to catheter assemblies and more particularly to over the needle catheter introducers for use in placing a catheter into a patient's blood vessel.

BACKGROUND OF THE INVENTION

Several techniques have been developed for the insertion of a catheter into a patient's blood vessel. On such technique is known as the Seldinger technique. The Seldinger technique involves the use of a needle which is initially advanced into an artery at a preferred angle of approximately 30 to 45 degrees. The puncture of the artery is confirmed by the presence of blood in the needle. Next, a flexible J-spring guidewire is inserted through the needle for approximately 15 to 20 cm. The needle is then withdrawn over the guidewire while pressure is applied to the artery to prevent the formation of a hematoma at the incision site. The guidewire is then cleaned with sterile saline and a multipurpose catheter is inserted over the guidewire until the catheter reaches the desired initial location. The guidewire is then removed from the inside of the catheter and the catheter is flushed to remove any thrombus material which may have been picked up as the catheter was inserted into the artery over the guidewire. Finally, the catheter is advanced to a final location such as in the ascending aorta.

In another catheter insertion technique, an introducer needle is inserted through a flexible cannula so that the needle point extends beyond the distal end of the cannula and so that the hub of the introducer needle engages the hub of the cannula. In this technique, the introducer needle and cannula are advanced through the skin of the patient so that the bevel on the distal end of the introducer needle pierces the patient's blood vessel at an angle of approximately 30 to 45 degrees. Once the introducer needle pierces the patient's blood vessel, the introducer needle is withdrawn and the cannula is advanced into the patient's blood vessel. Next, a flexible guidewire is inserted into the patient's blood vessel through the cannula. The cannula is then removed and a catheter is inserted into the patient's blood vessel over the guidewire. Finally, the guidewire is removed and the catheter is flushed to remove any thrombus material from the catheter.

Normally, during this procedure, the nurse must initially determine that the patient's blood vessel has been properly pierced and then while pressing on the patient's blood vessel to prevent the formation of a hematoma at the incision site, the nurse must single handedly separate the needle hub from the hub. During the insertion and removal of the introducer needle from the patient's blood vessel, it is very important that the nurse is aware of the orientation of the bevel on the distal end of the introducer needle to ensure that the blood vessel is not pierced again or that the cannula itself is not pierced if the needle hub and cannula hub are inadvertently separated during the insertion procedure. Additionally, by placing the projection on the proximal end of the cannula member, it is often times difficult to secure the cannula member to the skin of the patient if the nurse desires to insert the catheter at a later time.

A number of prior assemblies are known to facilitate the separation of the needle hub from the cannula hub. These prior assemblies typically include the use of a projection extending from the proximal end of the cannula hub. The projection on the cannula hub facilitates the separation of the needle hub from the cannula hub by providing a surface on the cannula hub which may be pressed against while the needle hub is firmly held by the nurse. Although this projection makes the single handed separation of the needle hub from the cannula hub easier, it may also cause the needle hub to be inadvertently separated from the cannula hub during the insertion procedure.

Many of the prior assemblies use a friction fit between the interior of the cannula hub and the exterior of the needle hub as the primary method of retaining the needle hub in the cannula hub. When the needle hub is separated from the cannula hub to remove the introducer needle from the patient's blood vessel, the cannula hub is often rotated to release the frictional fit between the needle hub and the cannula hub. During this procedure, it is important that the bevel on the distal end of the introducer needle remain oriented in the same position as when the blood vessel was initially pierced so that the blood vessel is not pierced a second time by movement of the introducer needle in the patient's blood vessel as the needle hub and cannula hub are separated. Therefore, although it is important to have a secure connection between the needle hub and the cannula hub during the insertion procedure, it is equally important that the needle hub and cannula hub are readily separable when the introducer needle is to be removed from the patient's blood vessel. None of the presently available devices meet this requirement.

It is apparent that a need remains in the art for an over the needle catheter introducer which will secure the needle hub to the cannula hub while the assembly is introduced into the patient's blood vessel and will readily release the cannula hub from the needle hub when the introducer needle is removed from the patient's blood vessel.

SUMMARY OF THE PRESENT INVENTION

An object of the present invention is to substantially overcome the disadvantages mentioned above.

A feature of the present invention is to provide a pair of luer type extensions on the proximal end of the cannula hub to facilitate the locking and release of the cannula hub from the needle hub.

Another feature of the present invention is the provision of a distally projecting locking groove on the distal side of a finger member on the needle hub to releasably engage a luer extension on the cannula hub.

A further feature of the present invention is the provision of a radially extending finger member on the cannula hub to facilitate the single handed separation of the needle hub from the cannula hub.

The present invention represents an improvement over the prior art by providing an introducer consisting of a needle hub and cannula hub which are readily locked during insertion of the assembly into the patient's blood vessel and which are readily separable to allow for the convenient removal of the introducer needle from the patient's blood vessel. Additionally, the finger member on the needle hub provides the nurse with an indicator of the orientation of the beveled distal end of the introducer needle within the patient's blood vessel.

In the preferred embodiment, the introducer consists of an introducer needle and a cannula member. The introducer needle consists of an elongate hollow needle having a beveled distal end and a needle hub on the proximal end thereof. The needle hub includes an axial bore extending therethrough, an outwardly extending finger member on the distal end thereof and a pair of gripping members extending lengthwise along the sides of the needle hub. The distal side of the finger member includes a distally extending groove member positioned above the reduced diameter bore extension of the needle hub to contact and engage the luer type extensions on the proximal end of the cannula hub.

The cannula member consists of an elongate flexible tubular member which is sized to slidingly fit over the introducer needle. The tubular member extends along the introducer needle to a location just proximal to the beveled distal end of the needle. The proximal end of the cannula member includes a cannula hub having an axial bore extending therethrough, a finger member and a pair of luer type extensions thereon. The finger member extends radially from the cannula hub at a position slightly proximal to the distal end of the cannula hub and is oriented in longitudinal alignment with the finger member on the needle hub in the locked position of the introducer. The luer type extensions are radially positioned on the distal end of the cannula hub to releasably contact the groove member on the needle hub.

An advantage of the present invention is that the needle hub and cannula hub are securely locked together during the insertion of the present invention into the patient's blood vessel.

Another advantage of the present invention is that the needle hub and cannula hub are readily separable to facilitate the removal of the introducer from the patient's blood vessel.

Further features and advantages of the present invention will become apparent from the following detailed description of the present invention which describes the preferred forms of the present invention.

BRIEF DESCRIPTION OF THE DRAWINGS

FIG. 2 is a side view of the present invention;

FIG. 3 is a top of the present invention;

FIG. 5 is a rear view of the introducer needle of the present invention;

DETAILED DESCRIPTION OF THE PREFERRED EMBODIMENT

Figure 1:
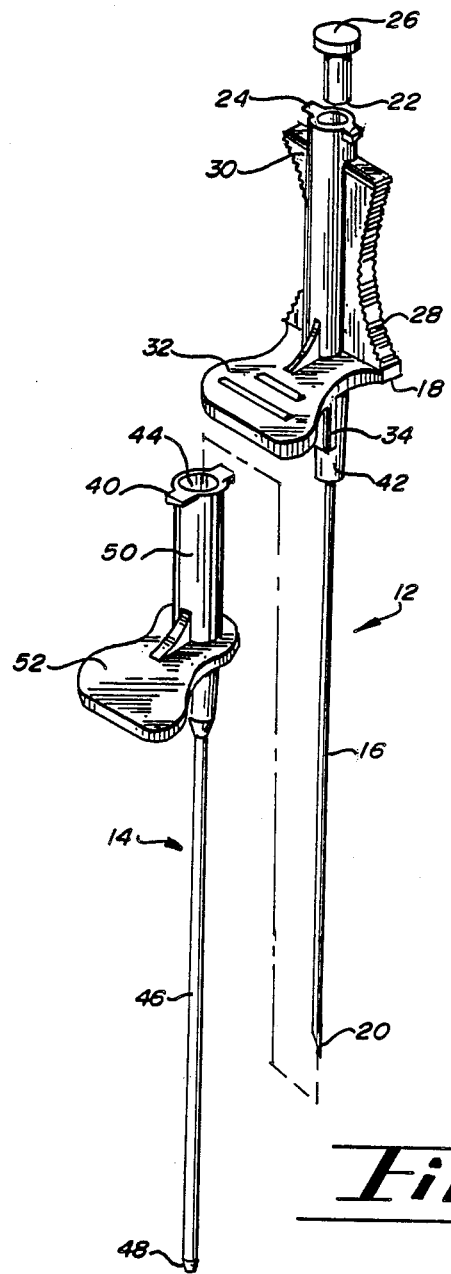
FIG. 1 is an exploded perspective view of the present invention.
Figure 4:
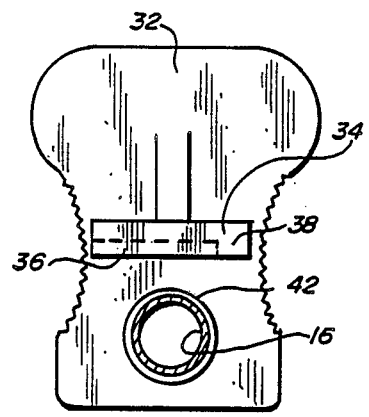
FIG. 4 is a frontal view of the introducer needle of the present invention.

In the preferred embodiment, the present invention is intended to be used as a conventional over the needle catheter introducer; however, it is readily anticipated that the present invention may also be used as a dilator to facilitate the insertion of larger diameter catheters into a patient's blood vessel.

In describing the present invention, the term "distal end" refers to the end of a part closest to the beveled needle point of the introducer. The term "proximal end" of a part refers to the end of a part furthest from the beveled needle point of the introducer.

The present invention is directed to an improved over the needle catheter introducer which is referred to herein generally as introducer 10. The introducer 10 consists of an introducer needle 12 and a cannula member 14.

The introducer needle 12 includes an elongate hollow metal needle section 16 and a needle hub 18. The distal end of the needle section 16 includes a beveled needle point 20 which is particularly oriented with a finger member 32 on the needle hub 18 so that the nurse can readily determine the orientation of the beveled needle point 20 at all times during the procedure.

The needle hub 18 is preferably an elongate plastic member which is rigidly attached to the proximal end of the needle section 16 and includes an axial bore 22 extending therethrough. The axial bore 22 includes an enlarged diameter proximal end which tapers to a smaller diameter area near the distal end of the needle hub 18 and then passes through the interior of the needle section 16. The proximal end of the needle hub 18 includes a pair of luer extensions 24 thereon which preferably have a luer lock angle of approximately 6 degrees so that nearly any other standard member may readily be attached thereto or so that the end cap 26 may be retained in the axial bore 22. A pair of grooved gripping members 28 and 30 are located longitudinally along the sides of the needle hub 18 to provide a convenient surface for the nurse to securely grasp the needle hub 18 during the insertion procedure.

A finger member 32 extends outwardly from the distal end of the needle hub 18. The finger member 32 is aligned with the beveled needle point 20 on the opposite longitudinal side of the needle section 16 to provide a readily observable indication of the relative orientation of the beveled needle point 20 in the patient's blood vessel. The distal side of the finger member 32 includes a distally extending groove member 34 which extends perpendicularly from the finger member 32. The groove member 34 includes a distal locking ridge 36 oriented parallel to and spaced apart from the finger member 32 and a perpendicular retaining ridge 38 along one side of the groove member 34. The locking member 36 and retaining ridge 38 create a grooved area on the bottom surface of the groove member 34 adjacent to the finger member to selectively retain one of the angled luer extensions 40 from the distal end of the cannula member 14 therein. A tapered bore extension 42 is positioned below the groove member 34 and extends distally from the distal end of the needle hub 18 to contact the interior surface of the axial bore 44 of the cannula member 14.

The cannula member 14 includes an elongate tubular member 46 which has an inner diameter substantially similar to the outer diameter of the needle section 16 and a cannula hub 50 with an axial bore 44 therethrough. The axial bore 44 of the cannula member 14 includes an enlarged diameter proximal end which tapers to a smaller diameter area near the distal end of the cannula hub 50 similar to the outside taper of the bore extension 42. The axial bore 44 continues from the distal end of the cannula hub 50 through the tubular member 46 and reduced diameter portion 48. The distal end of the tubular member 46 includes a tapered reduced diameter portion 48 which is positioned distally of the beveled needle point 20 in the locked position of the introducer 10. The proximal end of the cannula hub 50 includes a pair of luer extensions 40 which preferably have a luer lock angle of approximately 6 degrees. The finger member 52 is preferably located near the distal end of cannula hub 50 and extends radially from the cannula hub 50 in longitudinal alignment with the finger member 32 of the needle hub 18 when the introducer 10 is in the locked position. The location of the finger member 32 near the distal end of the cannula hub 50 allows the nurse a sufficient area on the proximal end of the cannula hub 50 to tape the proximal end of the cannula hub 50 to the skin of the patient if the catheter is to be inserted at a later time.

When the introducer 10 is assembled for insertion into the patient's blood vessel, the needle section 16 of the introducer needle 12 extends through the tubular member 46 of the cannula member 14 and the beveled needle point 20 of the needle section 16 extends distally a short distance beyond the reduced diameter portion 48 of the tubular member 46. The bore extension 42 on the distal end of the needle hub 18 extends into and sealingly contacts the inner surface of the axial bore 44 of the cannula member 14. One of the luer extensions 40 on the proximal end of the cannula member 14 is retained in the groove area formed by the finger member 32, the locking ridge 36 and the retaining ridge 38 so that the finger member 32 and locking ridge 36 prevent longitudinal movement of the luer extension 40 therein and the retaining ridge 38 prevents counterclockwise movement of the luer extension 40 therein. Therefore, once the introducer 10 has pierced the patient's blood vessel, the nurse may rotate the finger member 52 on the cannula member 14 clockwise to release the introducer needle 12 from the cannula member 14 so that the introducer needle 12 may then be withdrawn from the patient's blood vessel.

Figure 6:
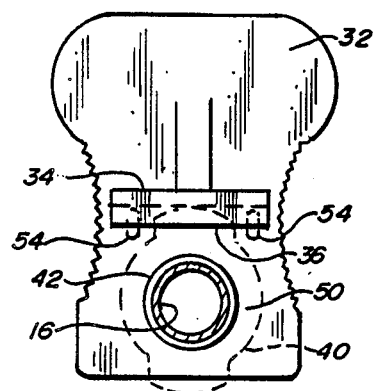
FIG. 6 is a frontal view of an alternate embodiment the introducer needle of the present invention.
Figure 7:
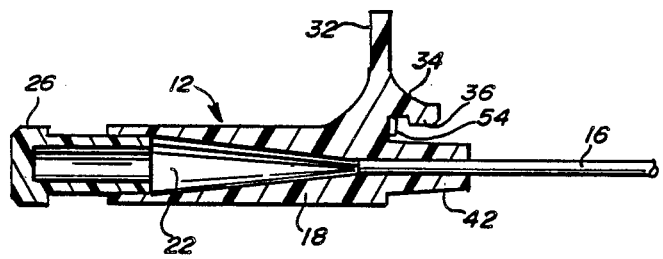
FIG. 7 is a cross-sectional view of the introducer needle illustrated in FIG. 6.

In the alternate embodiment illustrated in FIGS. 6 and 7, like numbers have been applied to like elements in order to illustrate the common elements of the respective embodiments. In this alternate embodiment, the distal side of the finger member 32 on the needle hub 18 includes a distally extending groove member 34 which extends substantially parallel to the bore extension 42 and axial bore 22. The bottom surface of the groove member 34 in this embodiment includes a locking ridge 36 which is parallel to and spaced apart from the finger member 32. A pair of lateral retaining lips 54 are oriented perpendicular to the finger member 32 and locking ridge 36 along the sides of the bottom surface of the groove member 34. As with the previous embodiment, the finger member 32 and the locking ridge 36 prevent longitudinal movement of the luer extension 40 in the groove area. The retaining lips 54 of this embodiment resist lateral movement of the luer extension 40 in the groove area but will allow the luer extension 40 to leave the groove area if the finger member 52 on the cannula member 14 is rotated while the finger member 32 on the introducer needle is held in position. Therefore, once the introducer 10 of this embodiment has pierced the patient's blood vessel, the nurse may rotate the finger member 52 clockwise or counterclockwise with respect to the finger member 32 so that the luer extension 40 passes over the retaining lip 54 and the introducer needle 12 may then be removed from the patient's blood vessel.

Next, in the preferred procedure as described above, the cannula member 14 is advanced into the patient's blood vessel and a standard guidewire (not shown) is inserted through the axial bore 44 of the cannula member 14 and into the patient's blood vessel. The cannula member 14 is then removed and a catheter (not shown) may be passed over the guidewire and advanced to the desired location in the patient's blood vessel. Finally, the guidewire is removed from inside the catheter and the catheter is flushed prior to use.

What is claimed is:

1. An over the needle catheter introducer comprising
a cannula member having an elongate tubular member and a cannula hub with an axial bore extending through said tubular member and said cannula hub;
an introducer needle having an elongate needle section and an needle hub;
said cannula hub having distal and proximal ends and a luer extension on said proximal end;
a finger member on said introducer needle extending radially therefrom generally perpendicular to said needle section;
a groove member extending distally from said finger member to releasably engage said luer extension therein when said introducer needle is inserted into said cannula member such that at least a portion of said needle section extends beyond said tubular member; and
said groove member including top and bottom surfaces and said bottom surface including a locking ridge and retaining means positioned distally of said finger means and wherein said locking ridge and said retaining means are oriented on said bottom surface of said groove member to limit the lateral and longitudinal movement of said luer extension in said groove member.

2. The introducer of claim 1, wherein said cannula member includes a finger member thereon extending outwardly from said cannula member and wherein said finger member on said cannula member is longitudinally aligned with said finger member on said introducer needle when said luer extension is engaged in said groove member.

3. The introducer of claim 1, wherein said locking ridge is oriented generally perpendicular to said retaining means on said bottom surface of said groove member.

4. An over the needle catheter introducer comprising
a cannula member having an elongate tubular member and a cannula hub with an axial bore extending through said tubular member and said cannula hub;
an introducer needle having an elongate needle section and an needle hub;
said cannula hub having distal and proximal ends and a luer extension on said proximal end;
a finger member on said introducer needle extending radially therefrom generally perpendicular to said needle section;
a groove member extending distally from said finger member to releasably engage said luer extension therein when said introducer needle is inserted into said cannula member such that at least a portion of said needle section extends beyond said tubular member;
wherein said groove member includes top and bottom surfaces and a locking ridge on the bottom surface thereof wherein said locking ridge is generally perpendicular to and spaced apart from said finger member to prevent the longitudinal movement of said luer extension from said groove member;
wherein said groove member further includes a retaining means on the bottom surface of said groove member oriented generally perpendicular to the locking ridge and finger member to limit lateral movement of said luer extension in said groove member.

5. An over the needle catheter introducer comprising
a cannula member having an elongate tubular member and a cannula hub with an axial bore extending through said tubular member and said cannula hub;
an introducer needle having an elongate needle section and an needle hub;
said cannula hub having distal and proximal ends and a luer extension on said proximal end;
a finger member on said introducer needle extending radially therefrom generally perpendicular to said needle section;
a groove member extending distally from said finger member to releasably engage said luer extension therein when said introducer needle is inserted into said cannula member such that at least a portion of said needle section extends beyond said tubular member;
wherein said groove member includes top and bottom surfaces and a locking ridge on the bottom surface thereof wherein said locking ridge is generally perpendicular to and spaced apart from said finger member to prevent the longitudinal movement of said luer extension from said groove member; and
wherein said groove member further includes a retaining means on the bottom surface of said groove member to prevent the rotational movement of the luer extension in at least one lateral direction.

6. The introducer of claim 1, wherein the distal end of the introducer needle includes a beveled needle point wherein the apex of the needle point is on the longitudinal side of the introducer needle opposite the finger member.

7. An over the needle catheter introducer comprising
a cannula member having distal and proximal ends and an elongate tubular member and a cannula hub with an axial bore extending through said tubular member and said cannula hub;
an introducer needle having distal and proximal ends and an elongate needle section and a needle hub with an axial bore extending through said needle section and said hub
a first finger member on said needle hub extending outwardly therefrom generally perpendicularly to the axial bore in said introducer needle;
a second finger member on said cannula hub extending outwardly therefrom generally perpendicular to the axial bore in said cannula member;
a luer extension extending radially from the proximal end of said cannula member;
a groove member extending distally from said first finger member and generally parallel to the axial bore of said needle introducer to releasably engage said luer extension therein when said introducer needle is inserted into said cannula member such that at least a portion of said needle section extends distally beyond the tubular member and wherein said first and second finger members are longitudinally aligned along the axial bore of said cannula member; and
said groove member including top and bottom surfaces and said bottom surface includes a locking ridge and at least one retaining means thereon oriented on said bottom surface of said groove member to limit the lateral and longitudinal movement of said luer extension in said groove member.

8. The introducer of claim 7, wherein said locking ridge is oriented generally perpendicular to said at least one retaining means on said bottom surface of said groove member.

9. An over the needle catheter introducer comprising
a cannula member having distal and proximal ends and an elongate tubular member and a cannula hub with an axial bore extending through said tubular member and said cannula hub;
an introducer needle having distal and proximal ends and an elongate needle section and a needle hub with an axial bore extending through said needle section and said hub
a first finger member on said needle hub extending outwardly therefrom generally perpendicularly to the axial bore in said introducer needle;
a second finger member on said cannula hub extending outwardly therefrom generally perpendicular to the axial bore in said cannula member;
a luer extension extending radially from the proximal end of said cannula member;
a groove member extending distally from said first finger member and generally parallel to the axial bore of said needle introducer to releasably engage said luer extension therein when said introducer needle is inserted into said cannula member such that at least a portion of said needle section extends distally beyond the tubular member and wherein said first and second finger members are longitudinally aligned along the axial bore of said cannula member;
wherein said groove member includes top and bottom surfaces and a locking ridge thereon oriented parallel to said first finger member to prevent the longitudinal movement of said luer extension from said groove member; and
wherein said groove member further includes a retaining ridge on the bottom surface thereof oriented generally perpendicular to said locking ridge and said first finger member to prevent the counterclockwise rotational movement of said luer extension from said groove member.

10. An over the needle catheter introducer comprising
a cannula member having distal and proximal ends and an elongate tubular member and a cannula hub with an axial bore extending through said tubular member and said cannula hub;
an introducer needle having distal and proximal ends and an elongate needle section and a needle hub with an axial bore extending through said needle section and said hub
a first finger member on said needle hub extending outwardly therefrom generally perpendicularly to the axial bore in said introducer needle;
a second finger member on said cannula hub extending outwardly therefrom generally perpendicular to the axial bore in said cannula member;
a luer extension extending radially from the proximal end of said cannula member;
a groove member extending distally from said first finger member and generally parallel to the axial bore of said needle introducer to releasably engage said luer extension therein when said introducer needle is inserted into said cannula member such that at least a portion of said needle section extends distally beyond the tubular member and wherein said first and second finger members are longitudinally aligned along the axial bore of said cannula member;

wherein said groove member includes top and bottom surfaces and a locking ridge thereon oriented parallel to said first finger member to prevent the longitudinal movement of said luer extension from said groove member; and wherein said groove member further includes at least one retaining lip on the bottom surface thereof oriented generally perpendicular to said locking ridge to limit the rotational movement of said luer extension from said groove member.

11. A method of inserting a catheter into a patient comprising the steps of inserting an introducer needle having distal and proximal ends thereon and an elongate needle section with a beveled distal needle point thereon and a needle hub with an outwardly extending finger member thereon wherein said finger member has a distally extending groove member thereon which is oriented parallel to an axial bore in said needle section into the axial bore of a cannula member having distal and proximal ends and an elongate tubular member and a cannula hub wherein the proximal end of the cannula hub has a luer extension extending radially therefrom;

rotating said cannula member about said introducer needle such that said luer extension is engaged in said groove member;

advancing the introducer needle and cannula member through the skin of a patient until the beveled distal needle point of the introducer needle pierces the blood vessel of the patient;

rotating the cannula member about said introducer needle such that said luer extension is released from said groove member;

withdrawing the introducer needle from the blood vessel of the patient and from the cannula member;

inserting a guidewire through the axial bore of the cannula member and into the blood vessel of the patient;

withdrawing the cannula member from the blood vessel of the patient and from around the guidewire;

inserting a catheter over the guidewire into the blood vessel of a patient; and withdrawing the guidewire from the blood vessel of a patient and from the catheter.

* * * * *